United States Patent
Batta et al.

(10) Patent No.: US 11,224,339 B2
(45) Date of Patent: Jan. 18, 2022

(54) DYNAMIC EYE CONDITION SELF-DIAGNOSIS

(71) Applicant: International Business Machines Corporation, Armonk, NY (US)

(72) Inventors: Raghav Batta, Ossining, NY (US); Elnatan Mataev, Poughkeepsie, NY (US); Heidi E Fritz, Raleigh, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 286 days.

(21) Appl. No.: 16/512,771

(22) Filed: Jul. 16, 2019

(65) Prior Publication Data

US 2021/0015357 A1    Jan. 21, 2021

(51) Int. Cl.
*A61B 3/032*    (2006.01)
*A61B 5/00*    (2006.01)
(Continued)

(52) U.S. Cl.
CPC ............ *A61B 3/032* (2013.01); *A61B 5/0077* (2013.01); *A61B 3/0008* (2013.01); *A61B 3/022* (2013.01); *A61B 3/024* (2013.01)

(58) Field of Classification Search
CPC ....... A61B 3/032; A61B 5/0077; A61B 3/024; A61B 3/022; A61B 3/0008
(Continued)

(56) References Cited

U.S. PATENT DOCUMENTS 5,880,702 A * 3/1999 Morimoto ............ G09G 3/2092
345/1.1
6,238,049 B1    5/2001 Griffin et al.
(Continued)

FOREIGN PATENT DOCUMENTS

CN    107124607    9/2017
CN    107659598 A    2/2018
(Continued)

OTHER PUBLICATIONS

Elliott et al., "Development of a Reading Speed Test for Potential-Vision Measurements," Investigative Ophthalmology & Visual Science, vol. 42, No. 8, Jul. 2001, pp. 1945-1949, 5 pages.
(Continued)

*Primary Examiner* — Mohammed A Hasan
(74) *Attorney, Agent, or Firm* — Amin, Turocy & Watson, LLP

(57) ABSTRACT

Facilitation of dynamic eye condition self-diagnosis is provided. A system can include a memory and a processor that executes computer executable components. The computer executable components can include: a status component that determines attributes of a user; a visualization component that generates a set of visualizations including at least one of: moving text, moving images or video; a test component that generates a set of tests using a subset of the set of visualizations; an assessment component that assesses an ability of the user to identify the subset of the set of visualizations displayed by the set of tests; and a vision scoring component that scores a vision of the user to generate a vision score, wherein the vision score is based upon an assessment of the ability of the user to identify the displayed subset of the set of visualizations and the attributes of the user.

20 Claims, 10 Drawing Sheets

(51) Int. Cl.
*A61B 3/024* (2006.01)
*A61B 3/02* (2006.01)
*A61B 3/00* (2006.01)

(58) Field of Classification Search
USPC .......................................................... 351/239
See application file for complete search history.

(56) References Cited

U.S. PATENT DOCUMENTS

| | | | |
|---|---|---|---|
| 7,350,921 | B2 | 4/2008 | Ridings |
| 7,367,675 | B2 | 5/2008 | Maddalena et al. |
| 2004/0105073 | A1 | 6/2004 | Maddalena et al. |
| 2006/0078858 | A1 | 4/2006 | Vroman et al. |
| 2008/0040719 | A1* | 2/2008 | Shimizu .............. G11B 20/18 718/102 |
| 2013/0141697 | A1* | 6/2013 | Berry .................... G16H 40/67 351/223 |
| 2014/0028973 | A1 | 1/2014 | Scolaro |
| 2017/0156585 | A1 | 6/2017 | Nie et al. |
| 2017/0181825 | A1* | 6/2017 | Hunter .................. A61B 5/067 |
| 2017/0311793 | A1 | 11/2017 | Green |
| 2017/0323485 | A1 | 11/2017 | Samec et al. |
| 2018/0168443 | A1 | 6/2018 | Inoue et al. |

FOREIGN PATENT DOCUMENTS

| | | |
|---|---|---|
| EP | 2710515 | 3/2014 |
| IN | 201841011158 | 9/2019 |
| WO | 2010132304 | 11/2010 |
| WO | 2012162205 | 11/2012 |
| WO | 2018046957 | 3/2018 |
| WO | 2018064052 | 4/2018 |

OTHER PUBLICATIONS

Ramulu et al., "Difficulty with Out-Loud and Silent Reading in Glaucoma," Investigative Ophthalmology & Visual Science, vol. 54, No. 1, Jan. 2013, pp. 666-672, 7 pages.

Fromer et al., "Are Individual Differences in Reading Speed Related to Extrafoveal Visual Acuity and Crowding?," PLOS One, DOI:10.1371/journal.pone.0121986, Mar. 19, 2015, 18 pages.

Walker et al., "The value of Tablets as reading aids for individuals with central visual field loss: an evaluation of eccentric reading with static and scrolling text," Ophthalmic & Physiological Optics, vol. 36, Issue 4, Jul. 2016, pp. 459-464, 6 pages.

Mell et al., "The NIST Definition of Cloud Computing," Recommendations of the National Institute of Standards and Technology, NIST Special Publication 800-145, Sep. 2011, 7 pages.

Appendix P—List of IBM Patents or Applications treated as related.

International Search Report and Written Opinion received for PCT application No. PCT/IB2020/056375 dated Oct. 21, 2020, 10 pages.

\* cited by examiner

DYNAMIC EYE CONDITION SELF-DIAGNOSIS

BACKGROUND

The subject disclosure relates generally to health diagnostics and, more particularly, to dynamic eye condition self-diagnosis.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, systems, computer-implemented methods, and/or computer program products provide dynamic eye condition testing tools for self-diagnosis.

Existing vision tests generally require a visit to a doctor or optometrist and consist of traditional vision charts consisting of rows of letters the alphabet of various sizes. The inconvenience caused by this requirement reduces the number of people who receive periodic eye examinations. Many individuals will only arrange for an eye examination if required to do so for purposes such as a job requirement or driver's license test or as a result of noticeable symptoms such as headaches or difficulty reading labels or distant signs. Vision loss can occur gradually, and many individuals do not notice vision impairment until it begins to significantly disrupt daily activities such as reading or driving. In addition, traditional tests administered by doctors and optometrists are limited to reading a static alphabet chart and thus may not provide a complete representation of a person's eyesight. Such tests do not test a person's ability to read text or identify objects in a dynamic environment that simulates everyday experiences in a complex world that places increasing demands on a person's eyesight. As a result, traditional eye tests can produce incomplete or flawed results that can produce dangerous results, such as licensing low vision drivers.

With recent advancements in computer-enabled graphics and mobile computing, various tools can be established that utilize such technology to enable a user to self-diagnose the condition of the user's eyesight. Such tools will enable users to quickly and efficiently determine if a visit to a doctor or optometrist is advisable or necessary or to discover potential issues with a user's eyesight that may not be discovered using a traditional eye examination.

In one or more embodiments, a system, a method and a computer program product are provided herein to enable users to self-diagnose eye conditions associated with a user's vision.

In accordance with an embodiment, a system comprises: a memory and a processor that executes computer executable components. The computer executable components can include a status component that determines attributes of a user, a visualization component that generates a set of visualizations including at least one of: moving text, moving images or video, a test component that generates a set of tests using a subset of the visualizations, an assessment component that assesses an ability of the user to identify the subset of the set of visualizations displayed by the set of tests, and a vision scoring component that scores a vision of the user to generate a vision score, wherein the vision score is based upon an assessment of the ability of the user to identify the displayed subset of the set of visualizations and the attributes of the user.

In accordance with another embodiment, a computer-implemented method comprises: determining, by a device operatively coupled to a processor, attributes of a user; generating, by the device, a set of visualizations including at least one of: moving text, moving images or video; generating, by the device, a set of tests using a subset of the visualizations; assessing, by the device, an ability of the user to identify the subset of the visualizations displayed by the set of tests; and scoring, by the device, a vision of the user to generate a vision score, wherein the vision score is based upon an assessment of the ability of the user to identify the subset of the visualizations and the attributes of the user.

In yet another embodiment, a computer program product comprises a computer readable storage medium having program instructions embodied therewith, the program instructions executable by a processor to cause the processor to: determine, by the processor, attributes of a user; generate, by the processor, a set of visualizations including at least one of: moving text, moving images or video; generate, by the processor, a set of tests using a subset of the set of visualizations; assess, by the processor, an ability of the user to identify the subset of the set of visualizations displayed by the set of tests; and score, by the processor, a vision of the user to generate a vision score, wherein the vision score is based upon an assessment of the ability of the user to identify the displayed subset of the set of visualizations and the attributes of the user.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Figure 1:
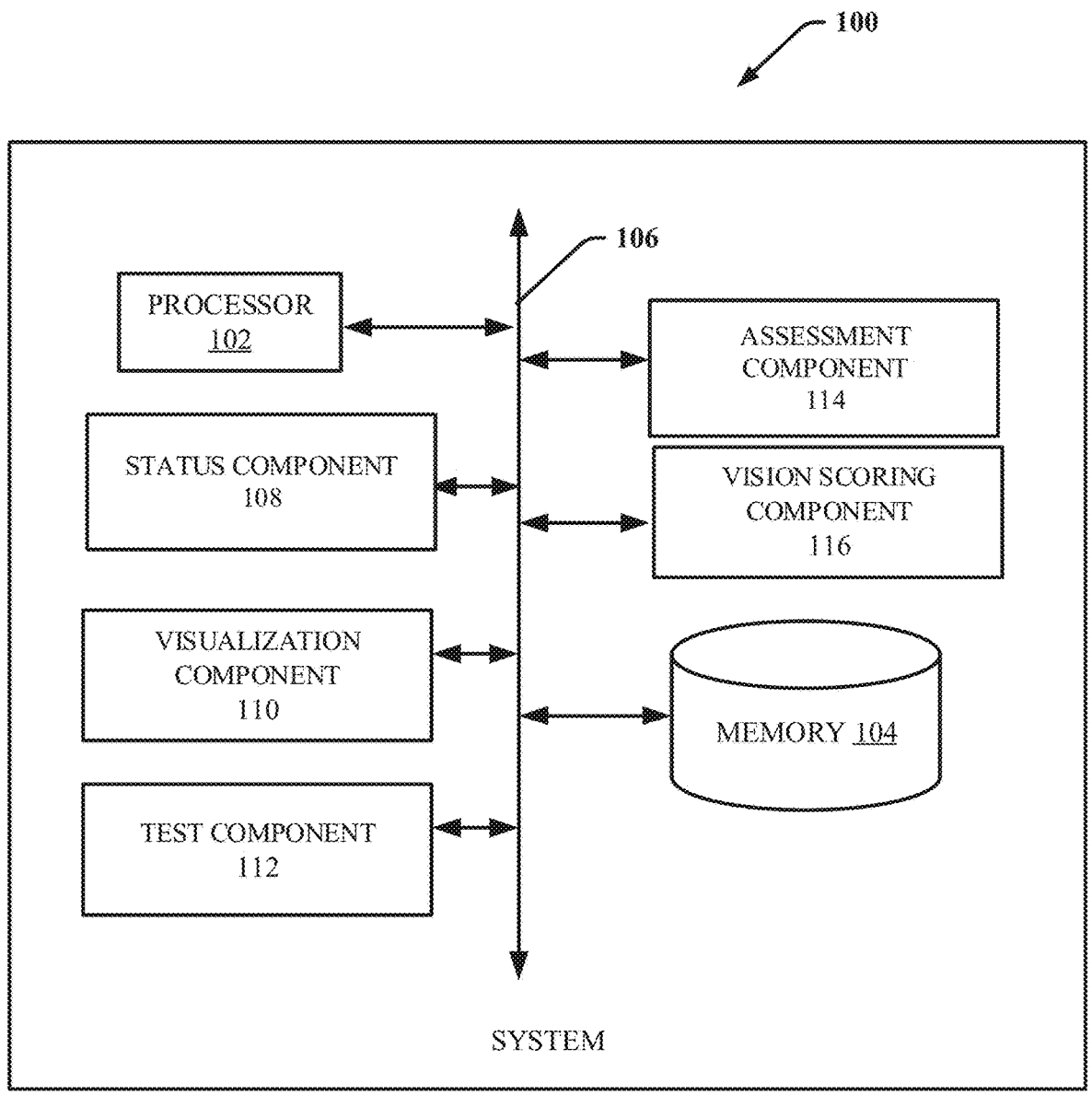
FIG. 1 illustrates a block diagram of a dynamic eye condition self-diagnosis system in accordance with one or more embodiments described herein.

Embodiments described herein include systems, methods, and computer program products that facilitate dynamic eye condition self-diagnosis. FIG. 1 illustrates a block diagram of an example of a dynamic eye condition self-diagnosis system 100 in accordance with one or more embodiments described herein. The system includes a processor 102, such as a computer, and a system memory 104. The system 100 can further include a system bus 106 that can couple various components, including, but not limited to, a status component 108, a visualization component 110, a test component 112, an assessment component 114 and a vision scoring component 116. The status component 108 determines attributes of a user. The visualization component 110 generates a set of visualizations including at least one of: moving text, moving images or video. The test component 112 generates a set of tests using a subset of the set of visualizations. The assessment component 114 assesses an ability of the user to identify the subset of the set of visualizations displayed by the set of tests. The vision scoring component 116 scores a vision of the user to generate a vision score, wherein the vision score is based upon an assessment of the ability of the user to identify the displayed subset of the set of visualizations and the attributes of the user.

In certain embodiments, the memory 104 can be contained in at least one of a cloud computing system or a user device such as a television, a desktop computer, a laptop computer, a tablet computer, a smartphone or the like.

In certain embodiments, the status component 108 determines attributes of a user. In one example, the status component 108 can include a questionnaire for a user to complete that includes questions about the user's age, other demographic information, previous eye conditions, use of corrective lenses, other medical history and other attributes that may be applicable to an eye condition diagnosis. In another example, some or all of a user's demographic or other relevant information can be obtained by the status component 108 through integration with an external system or database. For example, the status component 108 may receive information from sources such as a user's medical insurance carrier.

In certain embodiments, the visualization component 110 generates a set of visualizations including at least one of: moving text, moving images or video. In one example, the visualization component 110 can display subsets of visualizations on a variety of screens such as a television, a desktop computer, a laptop computer, a tablet computer, a touch screen, a smartphone or the like. In another example, the subsets of visualizations displayed by the visualization component 110 can vary with respect to attributes such as speed, size, placement on the screen, level of contrast or hue. In another example, video displayed by the visualization component 110 can include three-dimensional (3D) video.

In certain embodiments, the test component 112 generates a set of tests using a subset of the set of visualizations generated by the visualization component 110. In one example, the test component 112 can generate a set of tests including one or more of moving text, moving images or video presented at varying speeds, sizes, placements, levels of contrast or hues in order to test a user's vision capabilities. For example, the test component 112 can begin with one group of moving text from left to right followed by at least one additional group of moving text that is larger or smaller than the initial group of moving text. The test component 112 can progressively increase or decrease the size of moving text in order to determine the smallest size of moving text that can be identified by a user with respect to text moving from left to right. In another example, the test component 112 can generate tests that alter other variables of such moving text such as speed, placement, level of contrast or hue in order to test how other variables may affect the smallest size of moving text that can be identified by a user with respect to text moving from left to right.

In another example, the test component 112 can test a user's ability to identify objects or distinguish between similar objects controlling for attributes such as speed, size, placement, level of contrast or hue. In one example, the test component 112 can replicate set of tests using moving text delivered to a user with a set of tests using moving objects in order to confirm or supplement the results of the user's tests associated with moving text.

In another example, the test component 112 can test a user's ability to identify moving text or objects in the context of video. For example, tests relating to a user's ability to identify moving text of a certain size can be conducted by displaying store signs or street signs in the context of a video. In another example, tests associated with a user's ability to identify moving objects of a certain size can be conducted by displaying pedestrians or road hazards in the context of a video that simulates driving a vehicle. In another example, the test component 112 can generate tests that alter other variables of a video such as speed, placement of objects, level of contrast or hue in order to test how other variables may affect a user's ability to identify moving text or moving objects in different contexts that may affect a user's vision. In another example, tests generated by the test component 112 can include 3D video in order to test how a user's ability to identify moving text or objects in the context of video is affected by depth perception.

In another example, test component 112 can adapt a test to the profile of a user based upon the user's attributes determined by the status component 108. For example, a young person can read fewer words and recognizes fewer shapes and images than an older person. Thus, the tests generated by the test component 112 for a young person can be different than a test generated for an older person in order to better measure vision versus the understanding of words or the context of shapes and images. In another example, the test component 112 can target tests based upon cultural background. For example, users from large cities and users from rural areas have different levels of familiarity with respect to words, objects and settings. The test component 112 can vary the types of visualizations delivered in tests in order to test the extent to which familiarity with words, objects and settings may affect test results.

In another example, the questionnaire used by the status component 108 can include a question about a user's primary language and the user's proficiency in languages known by the user. For example, if the test component 112 includes text or moving text in English that tests a user's ability to read such text, the test component 112 can alter word combinations, topics and language in order reduce the influence of language comprehension on vision a user's test score. In another example, in cases where the status component 108 indicates a potential issue with a user's reading comprehension, the test component 112 can include a higher proportion of tests using objects versus text.

In another example, the test component 112 will indicate to a user the proper distance to maintain during tests between the user's eyes and the screen, which recommended distance will depend on the type of user device the user is using. For example, the recommended distance for tests on a television screen will be larger than the recommended distance for tests on a smartphone. In another example, if the user device is equipped with a camera facing a user, the test component 112 can monitor the distance between the screen and the user and notify the user when the recommended distance is not being maintained. Also, the actual distance measured by the test component 112 during tests can be another factor taken into account when scoring such tests.

In another example, the test component 112 can adapt the types, combination and size of visualizations delivered in tests depending on the size of the screen on a user device. For example, the test component 112 can deliver more visualizations and more combinations of visualizations on large screens such as televisions or desktop computer screens as opposed to a smartphone screen. In such cases, tests that place text or objects at the far end of the screen to test a wider scope of vision may be delivered by the test component 112 on larger screens such as a television or desktop computer screen but not on a smartphone screen. In another example, tests to determine a user's ability to read fine print at a close distance to simulate reading labels may be delivered by the test component 112 on a smartphone screen but not a television screen.

In another example, the test component 112 can receive answers from a user in a variety of forms depending on the controls available on a user device. For example, the test component 112 can enable a user to respond using a keyboard, touchpad, touch screen, stylus pen, mouse, game console controller, voice controls, gesture controls or the like.

In another example, the test component 112 can take into account whether a user is using corrective lenses during one or more tests. For example, tests for users who have been prescribed corrective lenses can be tailored to provide test results associated with that user's vision with and without corrective lenses. In one example, the test component 112 can introduce new tests with a question regarding whether a user is wearing corrective lenses. In another example, if the user device is equipped with a camera facing a user, the test component 112 can monitor the user to determine whether the user is wearing corrective lenses.

In another example, the number and combination of tests generated by the test component 112 for a user can be adjusted depending on the user's performance on the initial set of tests. For example, if a user is having difficulty reading words with text of a certain size and moving at a certain speed in the initial set of tests but can accurately identify objects of the same size moving at the same speed, the text component can generate additional tests with simpler words to address the possibility that reading comprehension is affecting test results versus eyesight limitations. The test component 112 can generate additional tests associated with any potential eyesight limitations revealed by previous tests in order to confirm or supplement such results from previous tests.

In certain embodiments, the assessment component 114 assesses an ability of the user to identify the subset of the set of visualizations displayed by the set of tests. In one example, the assessment component 114 can assess a user's ability to identify the subset of visualizations displayed by the set of tests delivered by the test component 112 as measured against vision standards currently used by doctors and optometrists. For example, the assessment component 114 can assess whether a user's performance on the tests indicates that the user may require corrective lenses based up vision standards currently used by doctors and optometrists. In another example, the assessment component 114 can control for certain attributes when assessing a user's ability to identify the subset of the visualizations displayed by the set of tests. For example, the assessment component 114 may place less emphasis on certain tests depending on a user's age, language skills or cultural background if other tests that minimize the influence of such factors generate different results. For example, a young person may not be able to identify moving text of a certain size due to comprehension issues but can consistently identify moving objects of the same size in a variety of contexts.

In another example, the assessment component 114 can utilize crowdsourced data to generate assessments. For example, the assessment component 114 can compare a user's performance on the set of tests generated by the test component 112 to a centralized database of other users of the system 100. Such database can include information associated with each user of the system 100 such as attributes determined by the status component 108 for each user, tests generated by the test component 112 and completed by each user, assessments generated by the assessment component 114 for each user or vision scores generated by the vision scoring component 116 for each user. The assessment component 114 can use such information to assess how a user with certain attributes compares to other users with similar attributes who completed similar tests. In another example, the assessment component 114 can utilize additional data associated with other users such as performance on conventional eye examinations by other users and any diagnosis associated with vision received by other users from a doctor or optometrist.

In certain embodiments, the vision scoring component 116 scores a vision of the user to generate a vision score, wherein the vision score is based upon an assessment of the ability of the user to identify the displayed subset of the set of visualizations and the attributes of the user. In one example, a vision score generated by the vision scoring component 116 will indicate the extent to which a user's vision has deficiencies that may require corrective lenses. The vision scoring component 116 may include a recommendation that the user visit a doctor or optometrist for a professional vision test. In another example, the vision scoring component 116 can provide a user a detailed report with a vision score for each aspect of the user's vision assessed by the assessment component 114. For example, such a report may indicate that a user has normal vision for moving text and moving video in all circumstances other than videos simulating driving at night. In another example, the vision scoring component 116 can provide a user a detailed report with a vision score for each aspect of the user's vision assessed by the assessment component 114 as compared to other users in similar demographic groups. For example, such a report may indicate that a user in his fifties has vision impairments that require a professional examination by a doctor or optometrist but has overall vision that is average for that user's age group. In another example, the vision scoring component 116 can provide a detailed comparison of a user's vision score compared to the results of any traditional eye examinations previously completed by the user. For example, this information may be useful to a doctor or optometrist in a reaching a more complete diagnosis that wouldn't not be possible with only the results of a traditional eye examination.

In another example, the vision score generated by the vision scoring component 116 can be displayed by the visualization component 110 in the form of one or more graphs, plots, graphics (e.g., graphics coded via display of one or more different hues) or the like in order to highlight one or more aspects of the vision score.

In certain embodiments, the vision scoring component 116 adjusts the vision score based on vision requirements associated with an activity or job. For example, occupations such as airline pilot or air traffic controller require higher vision standards and the vision score generated by the scoring component 116 can be adjusted to such higher standards. In another example, the test component 112 can generate tests tailored to simulate scenarios associated with an activity or job which may contribute to a more accurate or more detailed vision score generated by the vision scoring component 116 associated with that particular activity or job. For example, tests generated by the test component 112 for airline pilots can simulate the types and placements of instruments that an airline pilot would be required to read accurately at certain distances. In another example, tests generated by the test component 112 for law enforcement officers can test the extent to which a user can identify a smartphone as opposed to a weapon in the hands of an individual in various settings and distances. In another example, the test component 112 can generate tests tailored to certain types of activities. For example, the vision requirements for playing quarterback that require excellent peripheral vison are different than the vision requirements for hitting a small ball. Thus, tests generated by the test component 112 to measure vision for a specific type of activity can be tailored to the vision requirements associated with that activity. In these examples, the vision scoring component 116 can provide a detailed report that with a vision score for each aspect of the user's vision assessed by the assessment component 114 as compared to the vision requirements associated with an activity or job.

In another example, the vision scoring component 116 can highlight a user's aptitude to perform well at certain jobs or activities based upon a user's ability to excel at certain subsets of tests delivered by the test component 112.

In certain embodiments, the vision scoring component 116 adjusts the vision score based on vision characteristics associated with a disease or impairment. For example, certain diseases affecting eyesight cause symptoms related to specific areas of a person's field of vision such as peripheral vision or the center of the visual field. In one example, the vision scoring component 116 can organize test results based upon different areas of a user's field of vision. In another example, the vision scoring component 116 can highlight test results that may correlate to symptoms for a specific disease or impairment. For example, the vision scoring component 116 can highlight test results that indicate the inability to correctly identify certain hues.

In certain embodiments, the visualization component 110 can display subsets of visualizations utilizing an augmented reality component or virtual reality component. In one example, the visualization component 110 can display subsets of visualizations utilizing an augmented reality component contained in glasses worn by a user in order to overlay text or images onto the user's field of vision. For example, the visualization component 110 can overlay a sign on a building in a user's field of vision as a user is walking, enabling the test component 112 to test the user's ability to identify text of a certain size at a certain distance in the context of a dynamic, real world environment. In another example, the visualization component 110 can display subsets of visualizations utilizing a virtual reality component contained in a headset worn by a user that simulates the entire field of video the user would see when driving a car in order to measure peripheral vision. For example, the visualization component 110 can display moving objects in a user's peripheral vision using the virtual reality headset in order to test the user's ability to identify objects in the user's peripheral vision.

Figure 2:
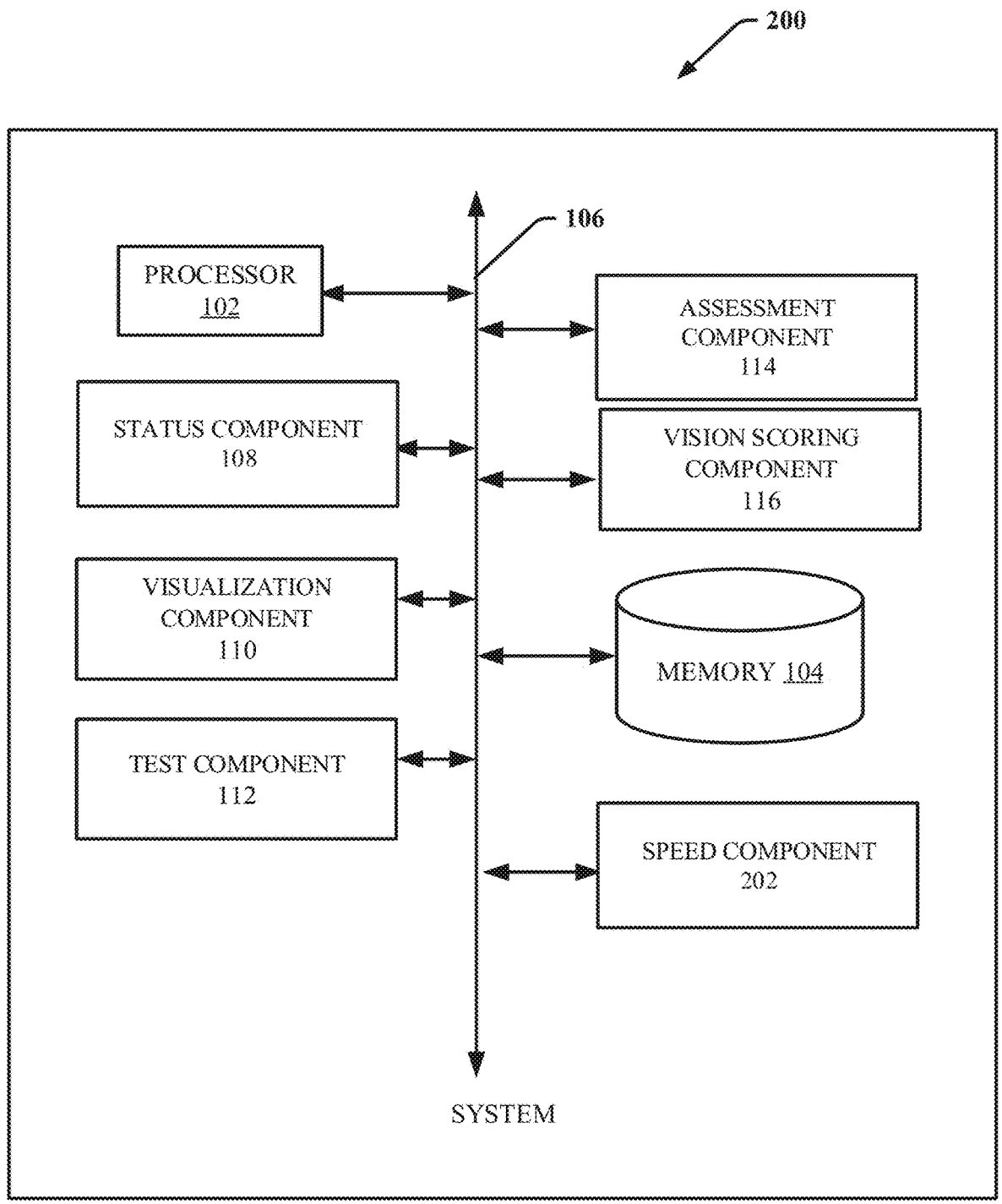
FIG. 2 illustrates a block diagram of another example of a dynamic eye condition self-diagnosis system in accordance with one or more embodiments described herein.

FIG. 2 illustrates a block diagram of another example of a dynamic eye condition self-diagnosis system in accordance with one or more embodiments described herein. Repetitive description of like elements employed in other embodiments described herein is omitted for sake of brevity.

In certain embodiments, the system 200 includes the speed component 202 that adjusts the speed of the set of tests delivered by the test component 112. In one example, the speed component 202 can progressively increase or decrease the speed of moving text of various sizes in order to identify the size and speed combinations that can be identified by a user with respect to text moving in a specific direction. In another example, the speed component 202 can progressively increase or decrease the speed of a moving object of various sizes in order to identify the size and speed combinations that can be identified by a user with respect to that object moving in a specific direction. In another example, the speed component 202 can progressively increase or decrease the speed of a video in order to test a user's ability to identify text and objects in the context of video played at different speeds.

Figure 3:
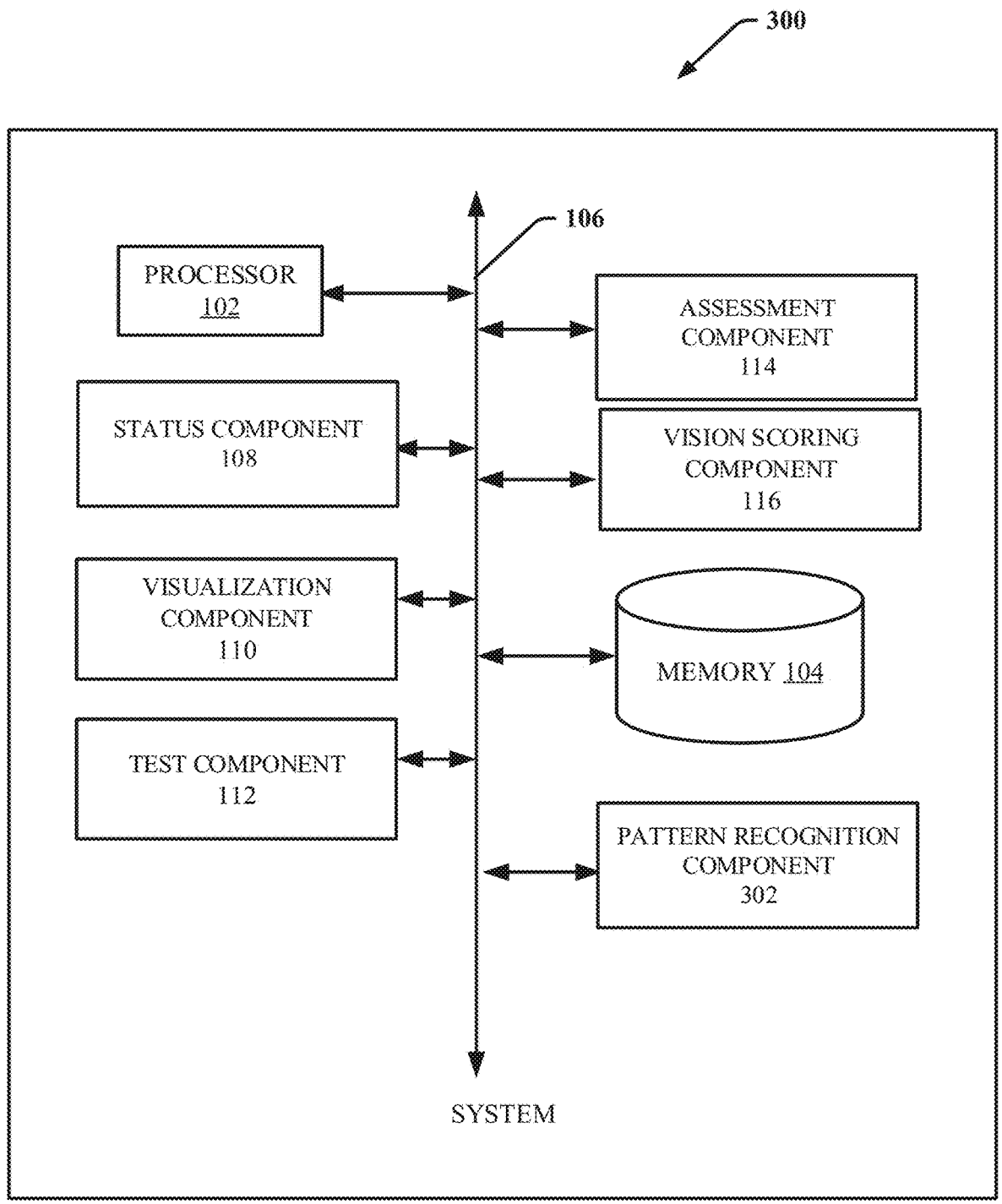
FIG. 3 illustrates a block diagram of yet another example of a dynamic eye condition self-diagnosis system in accordance with one or more embodiments described herein.

FIG. 3 illustrates a block diagram of yet another example of a dynamic eye condition self-diagnosis system in accordance with one or more embodiments described herein. Repetitive description of like elements employed in other embodiments described herein is omitted for sake of brevity. In certain embodiments, the system 300 includes the pattern recognition component 302 that analyzes facial expressions of a user as the user completes sets of tests delivered by the test component 112. In one example, if a user device is equipped with a camera facing a user, the pattern recognition component 302 can monitor facial expressions of a user and compare such expressions to a database of categorized facial expressions in order to determine the user's reactions that are not expressed by the user through the user device controls. For example, the pattern recognition component 302 can recognize a squinting expression which indicates that the user may be having difficulty seeing something on the screen clearly. In another example, the pattern recognition component 302 can recognize an expression that indicates the user may be confused by a test.

In another embodiment, the pattern recognition component 302 can analyze eye movement of a user as the user completes sets of tests delivered by the test component 302. In one example, if a user device is equipped with a camera facing a user, the pattern recognition component 302 can monitor the eye movement of a user to determine if or how quickly a user can identify text or an object on a particular spot on a screen. For example, the test component 112 may deliver a test that includes a video simulating the view of a driver in a vehicle in order to test the user's ability to detect moving objects in a variety of placements in the user's field of vision. In this example, the visualization component 110 can deliver subsets of visualizations on a television screen or virtual reality headset equipped with a camera that can enable the pattern recognition component 302 to monitor the eye movement of a user to determine if or how quickly a user can detect a deer in the user's peripheral vision running towards the road on which the vehicle is traveling.

Figure 4:
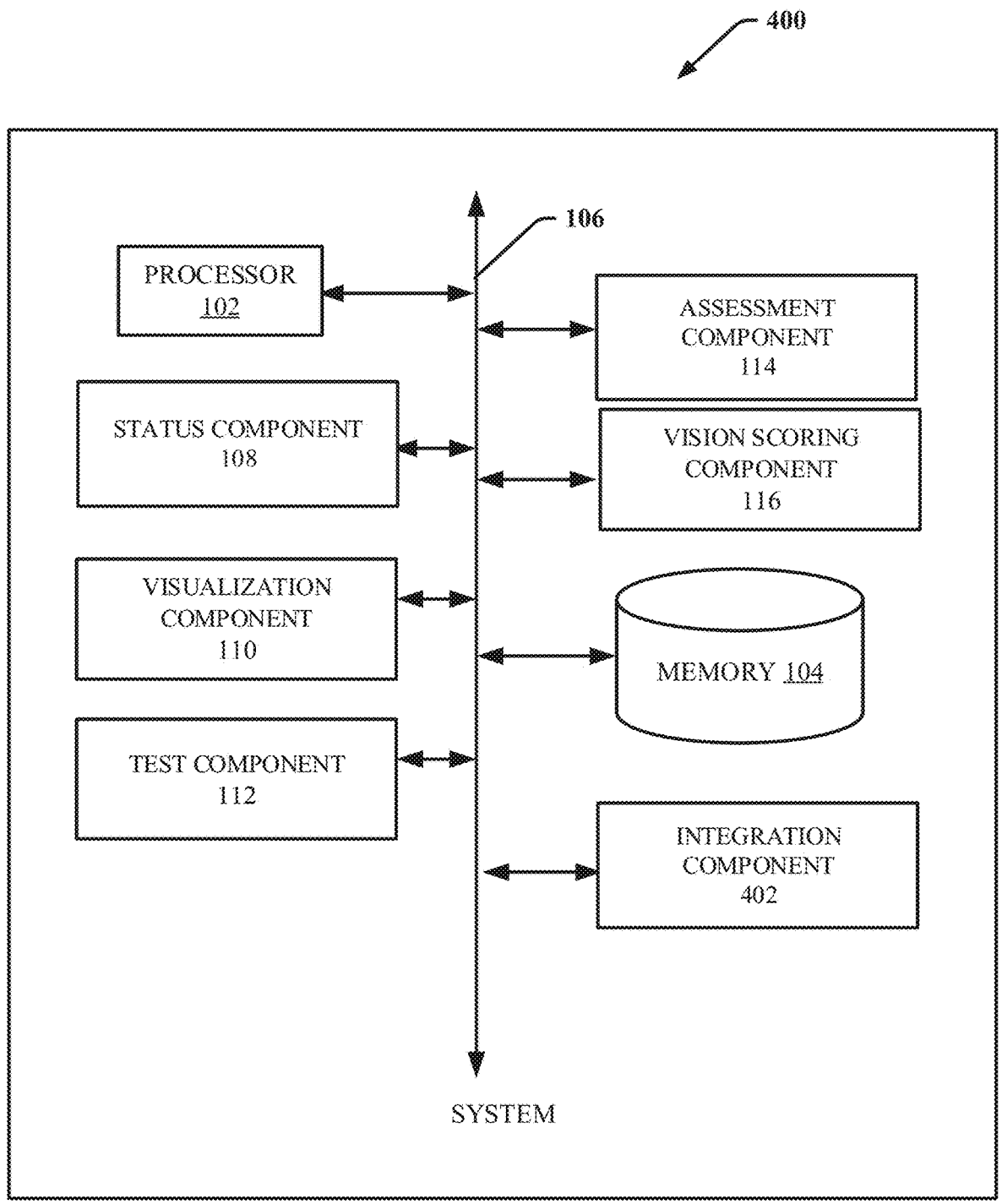
FIG. 4 illustrates a block diagram of yet another example of a dynamic eye condition self-diagnosis system in accordance with one or more embodiments described herein.

FIG. 4 illustrates a block diagram of yet another example of a dynamic eye condition self-diagnosis system in accordance with one or more embodiments described herein. Repetitive description of like elements employed in other embodiments described herein is omitted for sake of brevity. In certain embodiments, the system 400 includes the integration component 402 that integrates the system 400 with other visualization tools. For example, the system 400 can be integrated by the integration component 402 into other visualization tools such as a video game console. As a user is playing a game, the test component 112 can test the user's ability to identify certain text or objects that are integrated into the game, and the results of such tests can be used by the assessment component 114 to assess the user's vision. In another example, the system 400 can be integrated by the integration component 402 into a wireless mobile device such as a smartphone. For example, the system 400 can enable the test component 114 to conduct tests at any time a user is using the smart phone. For example, as a user uses the smartphone, the test component 112 can test the user's ability to identify certain text or objects that are displayed on the screen of the smartphone as the user interacts with the smartphone without prompting the user that the user is being tested.

In another embodiment, the integration component 402 can utilize the pattern recognition component 302 to analyze facial expressions or eye movement of a user as the user uses a device that enables tests through the integration component 402. For example, as a user uses a smartphone with tests delivered by the test component 114 enabled by the integration component 402, the pattern recognition component 302 can analyze whether the user is squinting or bringing the phone closer to the user's face when trying to read text of a certain size.

Figure 5:
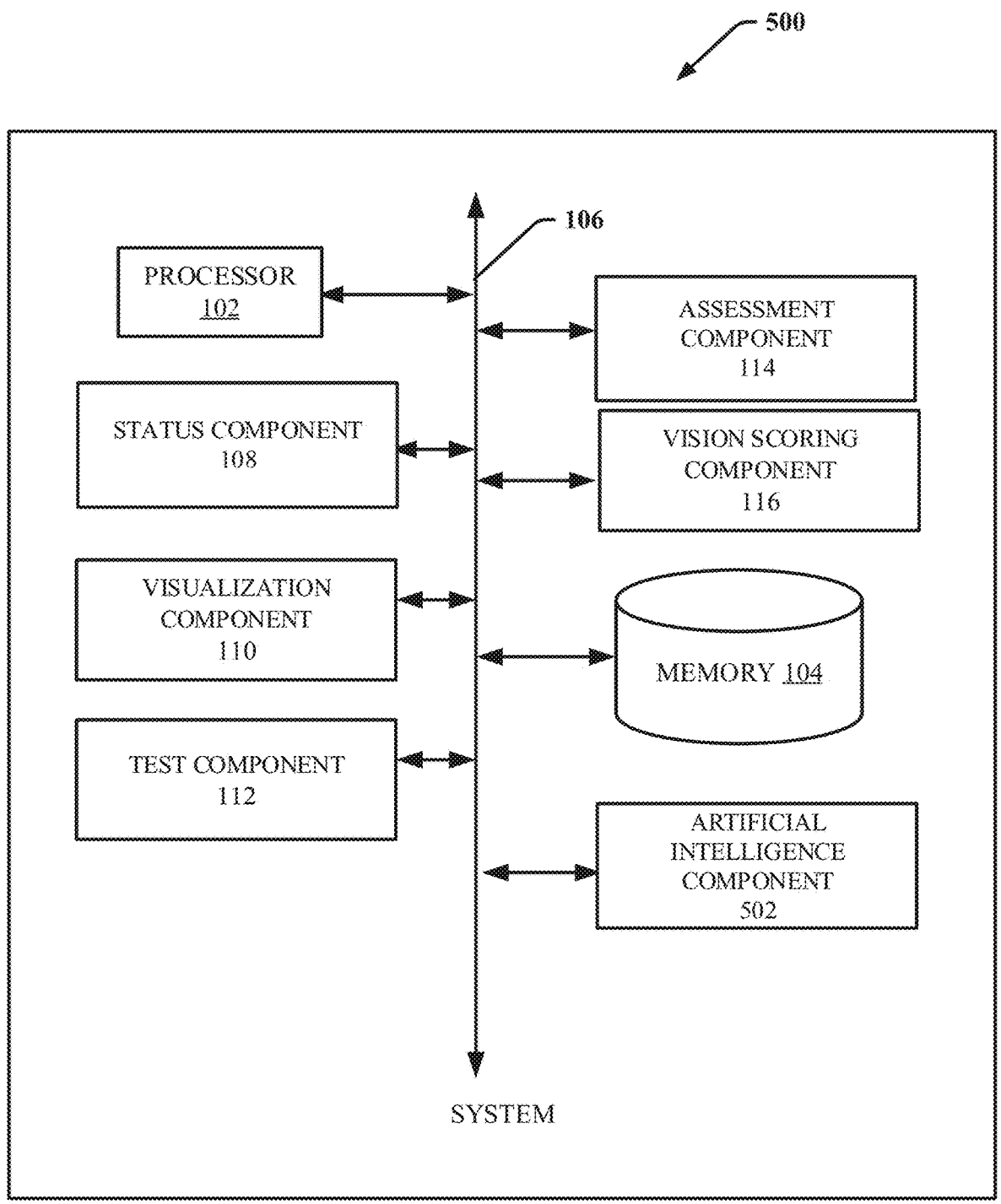
FIG. 5 illustrates a block diagram of yet another example of a dynamic eye condition self-diagnosis system in accordance with one or more embodiments described herein.

FIG. 5 illustrates a block diagram of yet another example of a dynamic eye condition self-diagnosis system in accordance with one or more embodiments described herein. Repetitive description of like elements employed in other embodiments described herein is omitted for sake of brevity. In certain embodiments, the system 500 includes the artificial intelligence component 502 that facilitates the determination of the vision score of a user. For example, the artificial intelligence component 502 can utilize artificial intelligence and machine learning to train one or more aspects of the system 500 to improve the accuracy of a user's vision score. In one example, the artificial intelligence component 502 can analyze the crowdsourced data collected from all users that have used the system 500 in order to detect correlations and trends that can be used to improve one or more aspects of the system 500. For example, the artificial intelligence component 502 may discover that users over the age of fifty with a particular demographic background have a higher than average likelihood of exhibiting a particular deficiency in their vision. In this case, the test component 112 can be adjusted by the artificial intelligence component 502 to supplement tests delivered to this subset of users in order to more thoroughly test for that potential deficiency. In another example, the artificial intelligence component 502 can analyze the crowdsourced data collected from all users that have used the system 500 together with feedback received after users have visited a doctor or an optometrist in order to detect correlations and trends that can be used to improve one or more aspects of the system 500.

For example, the artificial intelligence component 502 can determine the extent to which scores provided by the vision scoring component 116 to users are confirmed or contradicted by traditional eye tests administered by doctors or optometrists to such users. In this case, the test component 112, the assessment component 114 or the vision scoring component 116 can be adjusted by the artificial intelligence component 502 to account for such additional information. For example, if a certain test delivered by the test component 112 to a subset of users leads to incorrect vision scores delivered by the vision scoring component 116, such test can be deleted or modified by the artificial intelligence component 502 going forward for this subset of users. In another example, if the assessment component 114 consistently places less emphasis on certain tests associated with subsets of users due to age, language skills or cultural background, the artificial intelligence component 502 can delete or modify such tests going forward for this subset of users.

In another example, as more users complete tests that test the ability to distinguish between similar images, the artificial intelligence component 502 can train the test component 114 to use image comparisons that are more likely to generate accurate vision scores generated by the vision scoring component 116.

In another example, the artificial intelligence component 502 can utilize other data such as publicly available health and nutrition statistics in order to improve the system 500. For example, the artificial intelligence component 502 may detect trends or correlations that apply to a subset of users. In one example, tests of users using the system 500 may reveal a vision deficiency associated with one subset of users while health and nutrition statistics may indicate that such vision deficiency may have a correlation to an attribute not currently tracked by the status component 108. In such case the artificial intelligence component 502 can adjust the status component 108 to account for such attribute for such subset of users going forward.

In another example, the artificial intelligence component 502 can utilize artificial intelligence and machine learning to identify correlations that can predict the likelihood of future vision impairments for certain subsets of users.

In this regard, the artificial intelligence component 502 can perform classifications, correlations, inferences and/or expressions associated with principles of artificial intelligence. For instance, the artificial intelligence component 502 can employ an automatic classification system and/or an automatic classification. In one example, the artificial intelligence component 502 can employ a probabilistic and/or statistical-based analysis (e.g., factoring into the analysis utilities and costs) to learn and/or generate inferences. The artificial intelligence component 502 can employ any suitable machine-learning based techniques, statistical-based techniques and/or probabilistic-based techniques. For example, the artificial intelligence component 502 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the artificial intelligence component 502 can perform a set of machine learning computations. For example, the artificial intelligence component 502 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations.

Figure 6:
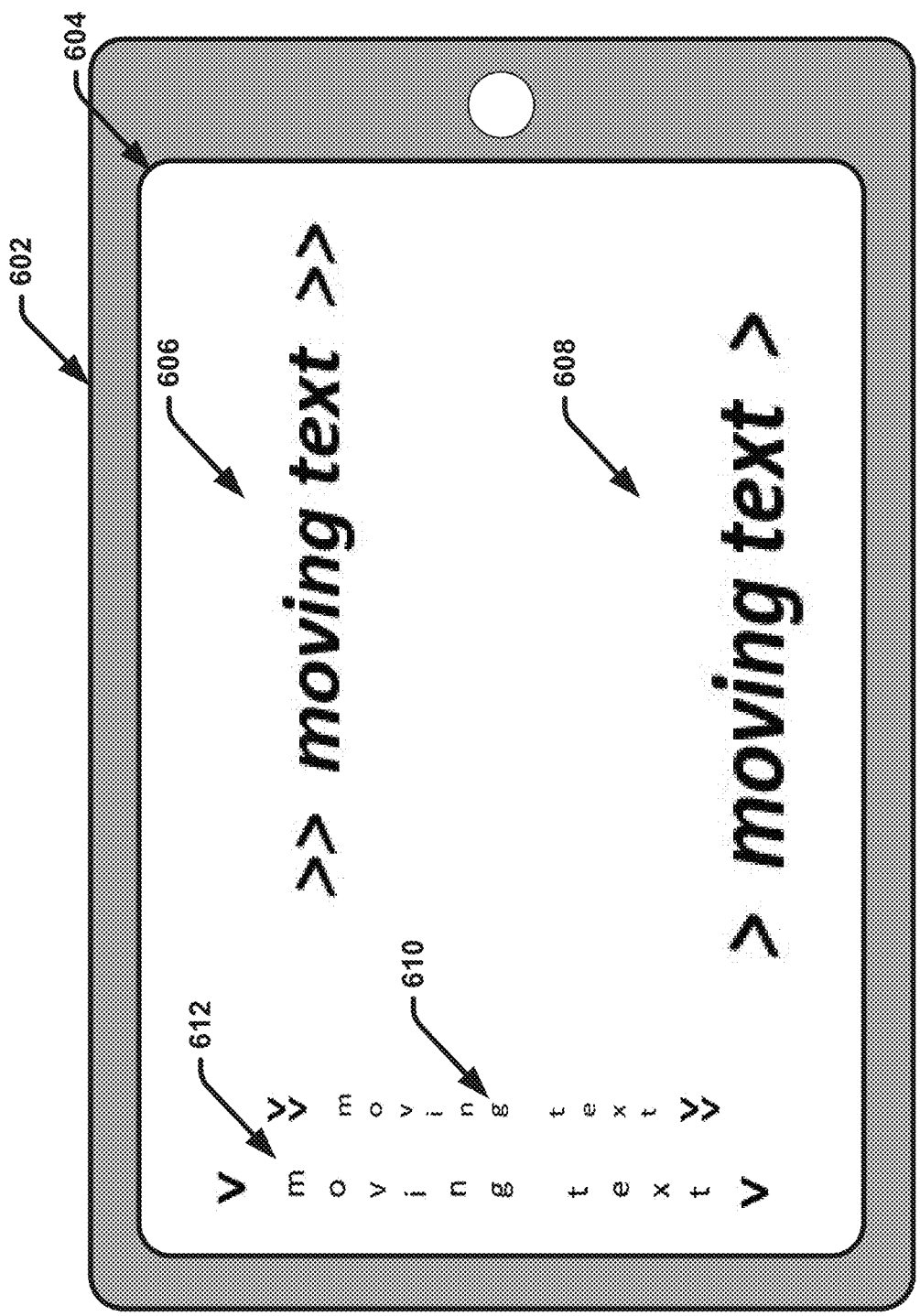
FIG. 6 illustrates yet another example of a dynamic eye condition self-diagnosis system in accordance with one or more embodiments described herein.

FIG. 6 illustrates yet another example of a dynamic eye condition self-diagnosis system in accordance with one or more embodiments described herein. Repetitive description of like elements employed in other embodiments described herein is omitted for sake of brevity. FIG. 6 depicts an example of a visualization component 110 in the form of a view of a tablet computer 602 with a large screen 604 in the center of the tablet computer 602. In this example, the subsets of visualizations generated by the test component 112 and displayed by the visualization component 110 include moving text in a variety of speeds, sizes and directions. For example, moving text 606 of a certain size is displayed by the visualization component 110 near the top of the screen moving substantially horizontally from left to right at a certain speed. In addition, moving text 608 of a larger size is displayed by the visualization component 110 near the bottom of the screen moving from left to right at a slower speed. This illustrates an example of how the test component 112 can offer moving text in various sizes, at various speeds and in different positions on a screen in order to test a user's ability to identify moving text. The speed component 202 can progressively increase or decrease the size or speed of moving text in order to identify the size and speed combinations that can be identified by a user with respect to text moving in a specific direction. Both moving text 606 and moving text 608 are included in FIG. 6 for demonstration purposes but can be delivered by the test component 112 one after another or at different points during a testing session in order to determine the vision capability of a user. In another example, moving text 610 of a certain size is displayed by the visualization component 110 on the left side of the screen moving substantially vertically from top to bottom at a certain speed. In addition, moving text 612 of a larger size is displayed by the visualization component 110 on the far-left side of the screen moving vertically from top to bottom at a slower speed. This further illustrates an example of how the test component 112 can offer moving text in various sizes, at various speeds and in different positions on a screen in order to test a user's ability to identify moving text.

Figure 7:
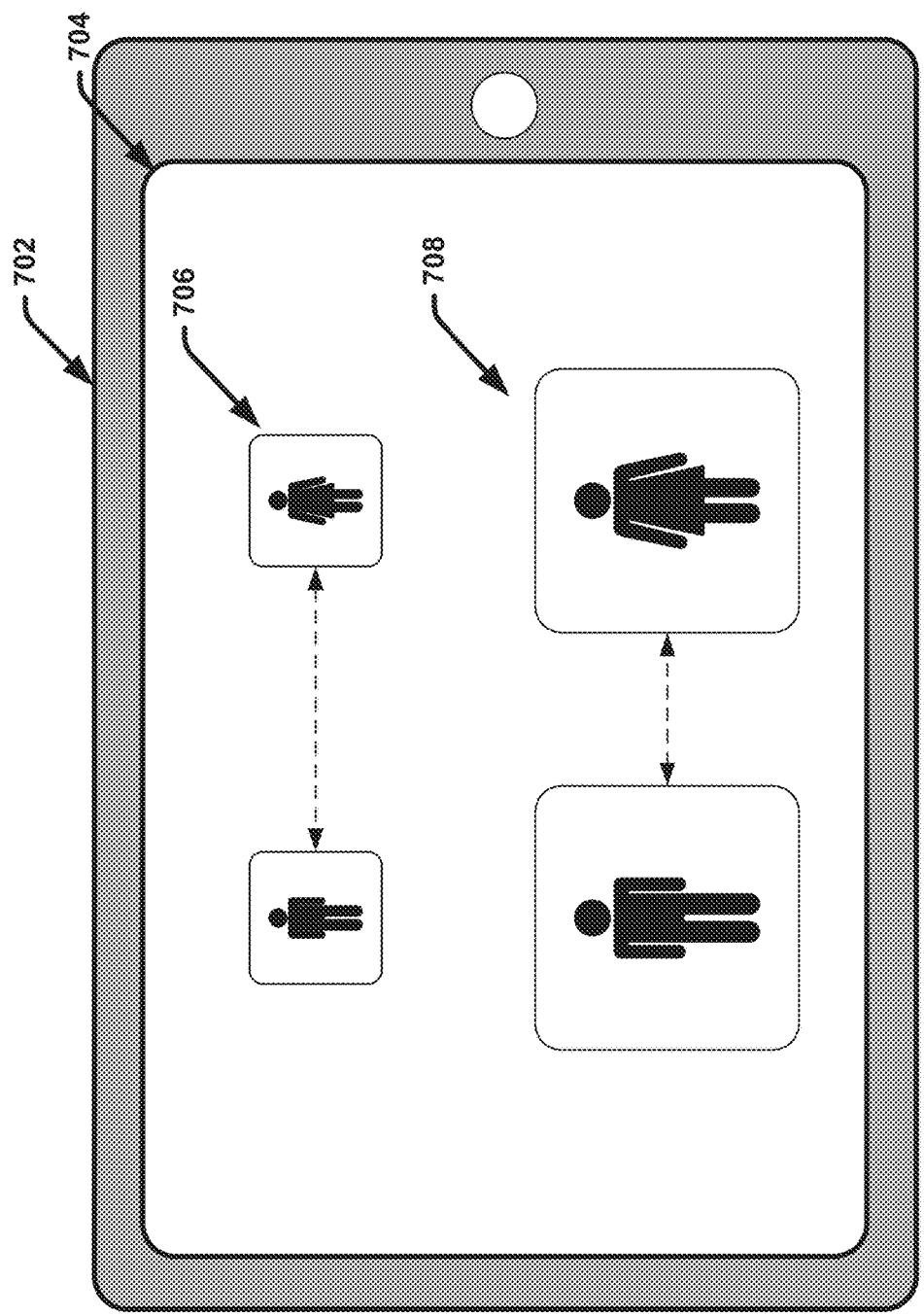
FIG. 7 illustrates yet another example of a dynamic eye condition self-diagnosis system in accordance with one or more embodiments described herein.

FIG. 7 illustrates yet another example of a dynamic eye condition self-diagnosis system in accordance with one or more embodiments described herein. Repetitive description of like elements employed in other embodiments described herein is omitted for sake of brevity. FIG. 7 depicts an example of a visualization component 110 in the form of a view of a tablet computer 702 with a large screen 704 in the center of the tablet computer 702. In this example, the subsets of visualizations generated by the test component 112 and displayed by the visualization component 110 include two similar images 706 and two larger versions of such similar images 708 that can be used to test the vision capabilities of a user. One of the two images would be presented to a user who would be prompted to identify the image. This illustrates an example of how the test component 112 can offer images in various sizes in order to test a user's ability to identify images of various sizes. The test component can progressively increase or decrease the size of images in order to identify the size that can be identified by a user. In another example, the test generated by the test component 112 can add variables such as movement in various directions, placement on the screen or placement within video to further test a user's ability to identify an object depending on context.

Figure 8:
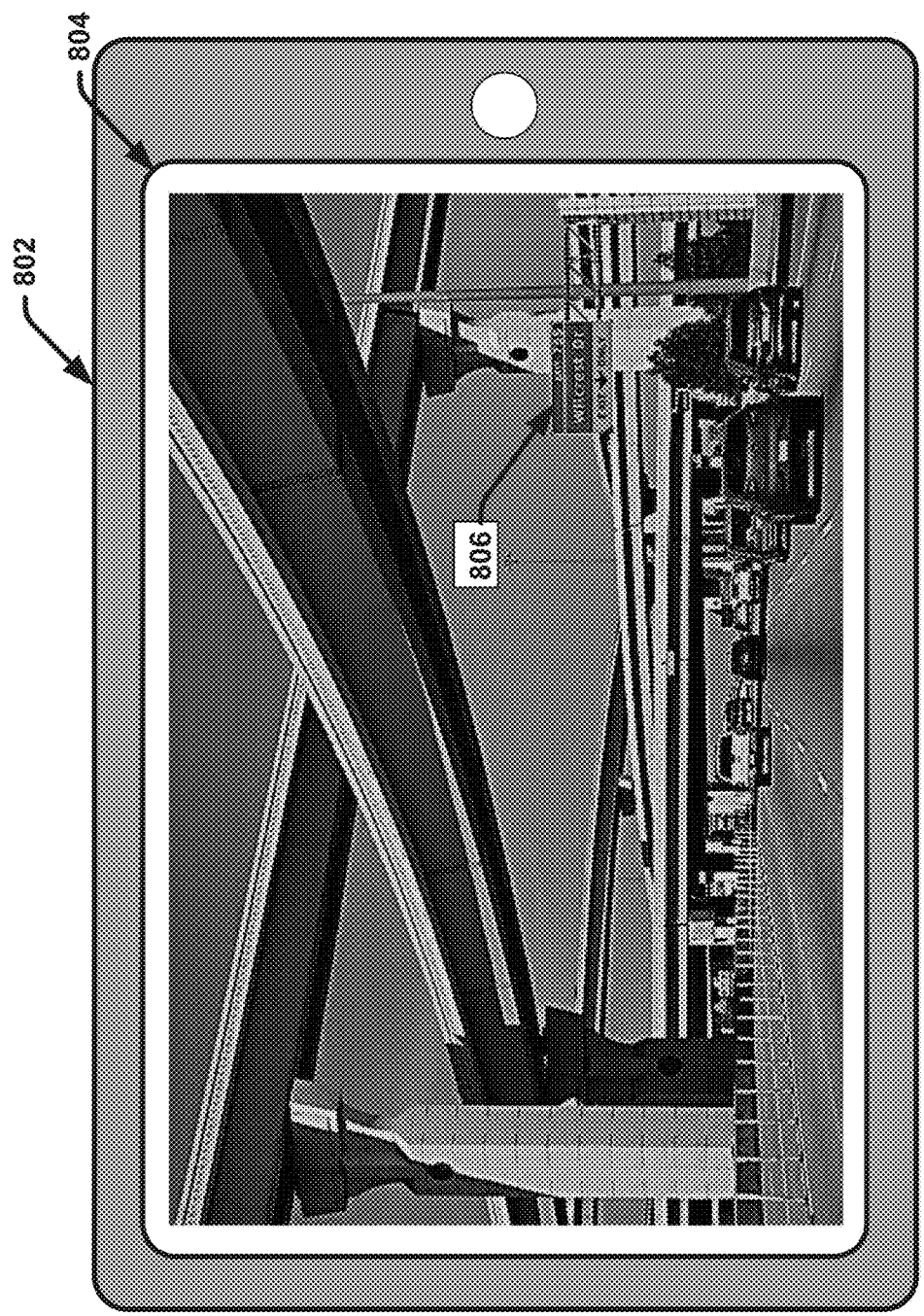
FIG. 8 illustrates yet another example of a dynamic eye condition self-diagnosis system in accordance with one or more embodiments described herein.

FIG. 8 illustrates yet another example of a dynamic eye condition self-diagnosis system in accordance with one or more embodiments described herein. Repetitive description of like elements employed in other embodiments described herein is omitted for sake of brevity. FIG. 8 depicts an example of a visualization component 110 in the form of a view of a tablet computer 702 with a large screen 704 in the center of the tablet computer 702. In this example, a single frame of a video is presented from the point of view of a driver in a vehicle as the vehicle travels on a freeway. An exit sign 806 is positioned on the right side of the road which can be used by the test component 112 to test a user's ability to read the oncoming sign. In another example, the test component 112 can include signs of various shapes, sizes and hues with the video simulating the vehicle traveling at various speeds in various light conditions in order to test a user's ability to read signs in a dynamic environment. In another example, a use can be tested on the user's ability to identify objects in lieu of reading signs.

Figure 9:
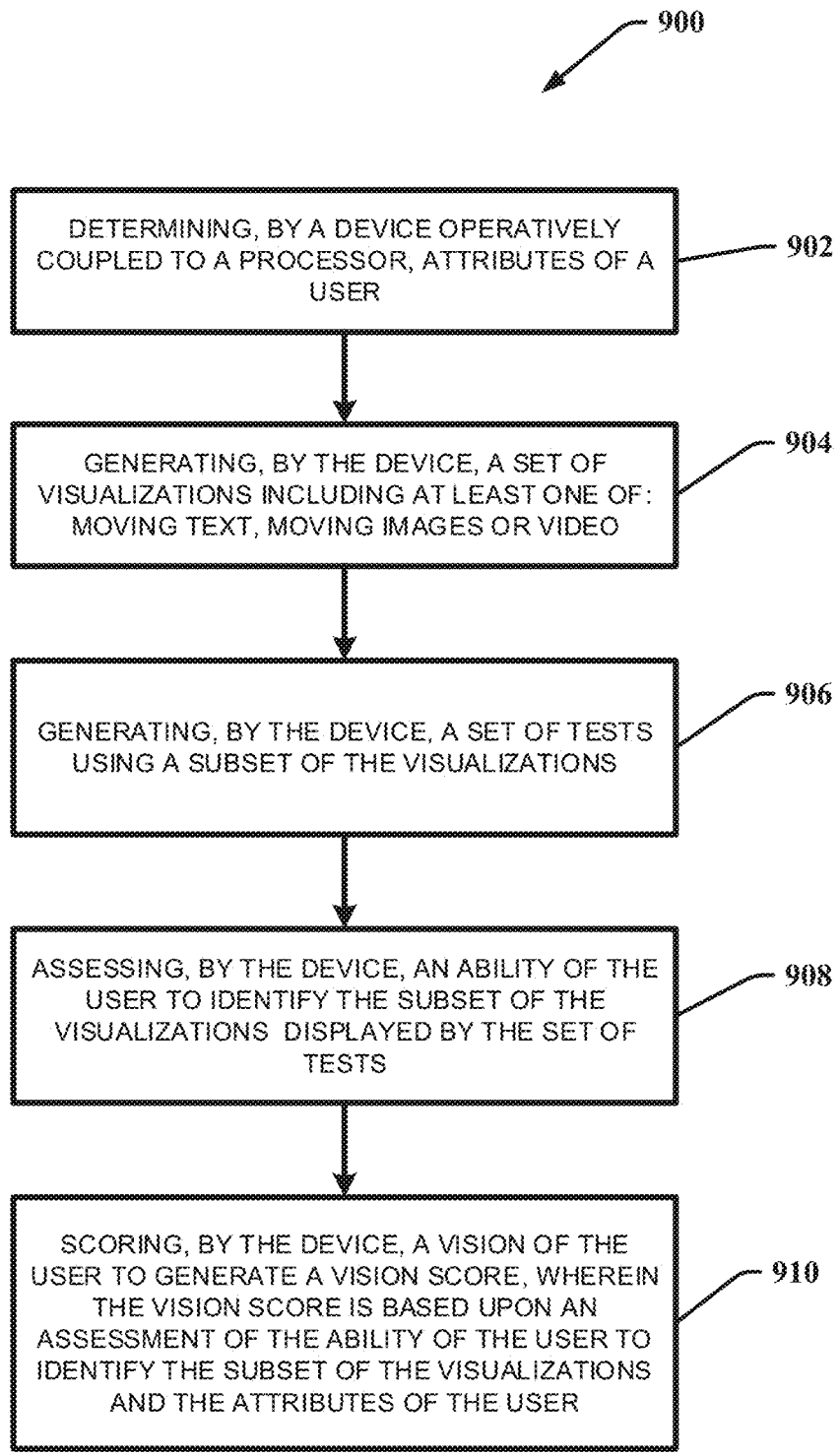
FIG. 9 illustrates a flow diagram of an example of a dynamic eye condition self-diagnosis computer-implemented method in accordance with one or more embodiments described herein.

FIG. 9 illustrates a basic method flowchart 900 of functional acts within various embodiments. Repetitive description of like elements employed in other embodiments described herein is omitted for sake of brevity. 902 represents a first act that includes determination of attributes of a user (e.g., via the status component 108). At 904, a set of visualizations including at least one of moving text, moving images or video are generated (e.g., via the visualization component 110). At 906, a set of tests are generated using a subset of the visualizations (e.g., via the test component 112). At 908, an ability of the user to identify the subset of the set of visualizations displayed by the set of tests is assessed (e.g., via the assessment component 114). At 910, a vision of the user is scored to generate a vision score, wherein the vision score is based upon an assessment of the ability of the user to identify the displayed subset of the set of visualizations and the attributes of the user (e.g., via the vision scoring component 116).

In certain embodiments, at step 910, the vision score is adjusted based on vision requirements associated with an activity or job. In another embodiment, at step 910, the vision score is adjusted based on vision characteristics associated with a disease or impairment. In another embodiment, at step 910, the vision score of a user is scored relative to a set of other users.

Figure 10:
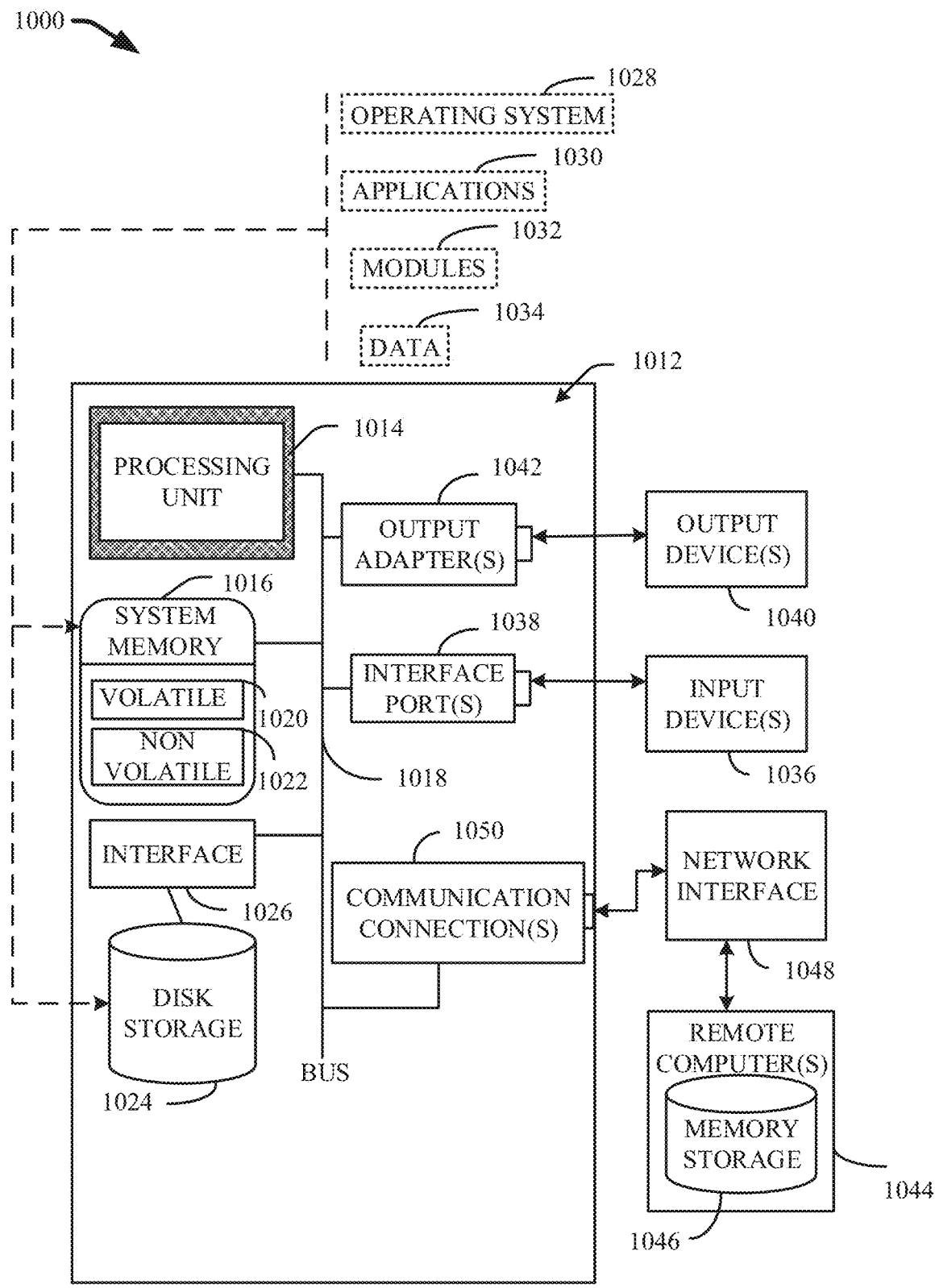
FIG. 10 is a schematic diagram of an example operating environment in accordance with one or more implementations described herein.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity.

With reference to FIG. 10, a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media. To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012.

System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising: a memory that stores computer executable components; a processor that executes computer executable components stored in the memory; a status component that determines attributes of a user; a visualization component that generates visualizations configured for vision testing, wherein the visualizations comprise moving text, moving images, or video; a test component that generates a set of tests using a subset of the visualizations; an assessment component that assesses an ability of the user to identify the subset of the visualizations displayed by the set of tests; and a vision scoring component that scores a vision of the user to generate a vision score, wherein the vision score is based upon an assessment of the ability of the user to identify the displayed subset of the visualizations and the attributes of the user.

2. The system of claim 1, wherein the vision scoring component adjusts the vision score based on vision requirements associated with an activity or job.

3. The system of claim 2, wherein the vision scoring component adjusts the vision score based on vision characteristics associated with a disease or impairment.

4. The system of claim 1, wherein the vision scoring component scores the vision score of the user relative to one or more other users.

5. The system of claim 1, further comprising a pattern recognition component that analyzes at least one of a facial expression or an eye movement of the user during testing.

6. The system of claim 1, further comprising an integration component that integrates the system with other visualization tools.

7. The system of claim 1, wherein the system employs crowdsourced data to facilitate the vision score of the user.

8. The system of claim 1, further comprising an artificial intelligence component that facilitates the determination of the vision score of the user.

9. The system of claim 1, wherein the visualization component comprises at least one of an augmented reality component or a virtual reality component.

10. The system of claim 6, wherein the integration component dynamically transitions and executes the system on a wireless mobile device.

11. The system of claim 1, comprising a speed component that adjusts speed of the set of tests.

12. A computer-implemented method comprising: determining, by a device operatively coupled to a processor, attributes of a user; generating, by the device, visualizations configured for vision testing, wherein the visualizations comprise moving text, moving images, or video; generating, by the device, a set of tests using a subset of the visualizations; assessing, by the device, an ability of the user to identify the subset of the visualizations displayed by the set of tests; and scoring, by the device, a vision of the user to generate a vision score, wherein the vision score is based upon an assessment of the ability of the user to identify the subset of the visualizations and the attributes of the user.

13. The computer-implemented method of claim 12, further comprising adjusting, by the device, the vision score of the user based on vision requirements associated with an activity or job.

14. The computer-implemented method of claim 13, further comprising adjusting the vision score based on vision characteristics associated with a disease or impairment.

15. The computer-implemented method of claim 13, further comprising scoring the vision score of the user relative to a set of other users.

16. The computer-implemented method of claim 13, further comprising analyzing at least one of facial expressions of the user or eye movement of the user during testing.

17. The computer-implemented method of claim 13, further comprising employing, by the processor, crowdsourced data to facilitate determination of the vision score.

18. A computer program product that facilitates dynamic eye condition self-diagnosis, the computer program product comprising a non-transitory computer readable medium having program instructions embodied therewith, the program instructions are executable by a processor to cause the processor to: determine, by the processor, attributes of a user; generate, by the processor, visualizations configured for vision testing, wherein the visualizations comprise moving text, moving images, or video; generate, by the processor, a set of tests using a subset of the visualizations; assess, by the processor, an ability of the user to identify the subset of the visualizations displayed by the set of tests; and score, by the processor, a vision of the user to generate a vision score, wherein the vision score is based upon an assessment of the ability of the user to identify the displayed subset of the visualizations and the attributes of the user.

19. The computer program product of claim 18, further comprising program instructions executable by the processor to cause the processor to adjust a speed of the tests.

20. The computer program product of claim 18, further comprising program instructions executable by the processor to cause the processor to:
  employ, by the processor, crowdsourced data to facilitate determination of the vision score; and
  adjust, by the processor, the vision score of the user based on vision requirements associated with an activity or job.

* * * * *